US008063269B2

(12) United States Patent
Shah et al.

(10) Patent No.: US 8,063,269 B2
(45) Date of Patent: Nov. 22, 2011

(54) TRANSGENIC PLANTS WITH REDUCED LEVEL OF SATURATED FATTY ACID AND METHODS FOR MAKING THEM

(75) Inventors: Salehuzzaman Shah, Edmonton (CA); Randall Weselake, Edmonton (CA)

(73) Assignee: Alberta Research Council Inc., Edmonton, AB (CA)

(*) Notice: Subject to any disclaimer, the term of this patent is extended or adjusted under 35 U.S.C. 154(b) by 1058 days.

(21) Appl. No.: 10/583,301

(22) PCT Filed: Dec. 17, 2004

(86) PCT No.: PCT/CA2004/002156
§ 371 (c)(1),
(2), (4) Date: Jun. 11, 2007

(87) PCT Pub. No.: WO2005/059140
PCT Pub. Date: Jun. 30, 2005

(65) Prior Publication Data
US 2008/0092254 A1   Apr. 17, 2008

(30) Foreign Application Priority Data
Dec. 18, 2003 (CA) .................................... 2450000

(51) Int. Cl.
*A01H 5/00* (2006.01)
*C12N 15/82* (2006.01)
*C07H 21/04* (2006.01)
(52) U.S. Cl. ............... 800/298; 800/281; 435/320.1; 435/419; 536/23.1
(58) Field of Classification Search .................. None
See application file for complete search history.

(56) References Cited

U.S. PATENT DOCUMENTS

| 5,552,306 A | 9/1996 | Thomas et al. |
| 5,614,393 A | 3/1997 | Thomas et al. |
| 5,663,068 A | 9/1997 | Thomas et al. |
| 5,689,050 A | 11/1997 | Thomas et al. |
| 5,789,220 A | 8/1998 | Thomas et al. |
| 6,043,411 A | 3/2000 | Nishizawa et al. |
| 6,355,861 B1 | 3/2003 | Thomas |
| 6,683,232 B1 | 1/2004 | Thomas |
| 2003/0054521 A1 | 3/2003 | Booth et al. |
| 2004/0078845 A1 | 4/2004 | Thomas |

FOREIGN PATENT DOCUMENTS

| WO | WO9621002 A2 | 4/1996 |
| WO | WO 00/11012 A1 | 3/2000 |
| WO | WO 2004057001 A2 | 7/2004 |

OTHER PUBLICATIONS

Chinese Application No. 200480041766.9 Office Action with Translation for dated Feb. 13, 2009.
Chinese Office Action dated Apr. 13, 2010 received in related Chinese Patent Application No. 200480041766.9.
Barton, K.A., et al. "Regeneration of Intact Tobacco Plants Containing Full Length Copies of Genetically Engineered T-DNA, and Transmission of T-DNA of R1 Progeny." *Cell* (1983) vol. 32: 1033-1043.
Bellucci, Michele, et al. "Expression maize γ-zein and β-zein genes in Transgenic *Nicotiana tabacum* and *Lotus corniculatus*." *Plant Cell Tissue and Organ Culture* (2000) vol. 62: 141-151.
Bevan, Michael, "Binary *Agrobacterium* Vectors for Plant Transformation." *Nucl. Acids. Res.* (1984) vol. 12 No. 22: 8711-8721.
Dellaporta S.L., et al. "A plant DNA Mini-Preparation: Version II." (1983) *Plant Mol Biol Rep* vol. 1: 19-21.
Ditta, M.J., et al., "Broad Host Range DNA Cloning System for Gram-Negative Bacteria: Construction of a Gene Bank of *Rhizobium meliloti*." *Proc Natl Acad Sci.* U.S.A. vol. 27: 7347-7351.
Draper, J., et al., "Plant Genetic Transformation and Gene Expression; A Laboratory Manual", Eds. Blackwell Scientific Publications, 1988. Chapter 2 and Chapter 3.
Frammond, A.J., et al., "Mini-Ti: A New Vector Strategy for Plant Genetic Engineering."*Bio/Technology* (1983) vol. 1: 262-269.
Fraley, Robert T., et al. "The SEV System: A New Disarmed Ti Plamid Vector System for Plant Transformation." *Bio/Technology* (1985) vol. 3: 629-635.
Hahn JJ., et al., "Growth Kinetics, Nutrient Uptake, and Expression of the *Alcaligenes eutrophus* poly(β-hydroxybutyrate) Synthesis Pathway in Transgenic Maize Cell Suspension Cultures." *Biotech Prog* (1997) vol. 13: 347-354.
Hernalsteens, Jean-Pierre. "The *Agrobacterium tumefaciwns* Ti Plasmid as a Host Vector System for Introducing Foreign DNA in Plant Cells." *Nature* (1980) vol. 287: 654-656.
Hoekema, A., et al., "A Binary Plant Vector Strategy Based on Separation of *vir*- and t-Region of the *Agrobacterium tumefaciens* Ti-Plasmid." *Nature* (1983) vol. 303: 179-180.
Horsch, R.B., et al., "Leaf Disc Transformation." *Plant Molecular Biology Manual* (1988), A5/I-AF/9, Kluwer Academic Publishers, Dordrecht/Boston/London.
Ishizaki-Nishizawa O, et al., "Low-Temperature Resistance of Higher Plants is Significantly Enhanced by a Nonspecific Cyanobacterial Desaturase." *Nature Biotechnology* (1996) vol. 14:1003-1006.
Lehmann K., et al., *Plant Physiol.* (2001) Oct; vol. 127 No. 2: 436-49.
Manubu, Murakami, et al., "Genomic Organization and Functional Analysis of Murine PKD2L1." *J. Biol. Chem.* (2005) vol. 280 No. 7:5626-35.

(Continued)

*Primary Examiner* — Elizabeth McElwain
(74) *Attorney, Agent, or Firm* — Kilpatrick Townsend & Stockton LLP

(57) ABSTRACT

The present invention provides transgenic plants with reduced levels of saturated fatty acids in the seed oil and methods of making these plants. The transgenic plants developed through this method contain reduced levels of saturated fatty acids in seed oil due to expression of a prokaryotic delta-9 desaturase enzyme (i.e. an enzyme that introduces cis double bonds at the delta-9 position of saturated fatty acids) operably linked with an endoplasmic reticulum retention and retrieval signal sequence. One example of the invention is a plant expressing a heterologous delta-9 desaturase enzyme from cyanobacterium *Anacystis nidulans*, which converts lipid-bound 16:0 and 18:0 fatty acids into corresponding 16:1 and 18:1, in operative linkage with a KKSS (SEQ ID NO:5) endoplasmic reticulum retention and retrieval signal sequence.

9 Claims, No Drawings

OTHER PUBLICATIONS

Matzke, M.A., et al., "Transcription of Zein Gene Introduced into Sunflower Using Ti Plasmid Vector." *The EMBO Journal* (1984) vo. 3. No. 7: 1525-1531.

Michaelis, et al. *Ann. Rev. Mictobiol.* (1982) vol. 36:425-464.

Moloney, M., et al., "High Efficiency Transformation of *Brassica napus* using *Agrobacterium* Vectors." *Plant cell Rep* (1989) vol. 8: 238-242.

Sambrook, J., et al., "Molecular Cloning: A Laboratory Manual", (1989) Cold Spring Harbor Laboratory Press, Cold Spring Harbor, N.Y. vol. 2: 9.47-9.58.

Schardl C.L.,et al., "Design and Construction of a Versatile System for the Expression of Foreign Genes in Plants." *Gene* (1987) vol. 61: 1-11.

Shah S., et al., "Farming for the Future, AARI Project #19990032, Final Report", (2003) pp. 1-82.

Shasany AK, et al., *Indian J. Exp Biol* Apr. 2000; vol. 38 No. 4: 363-72.

Van Den Broeck, et al., "Targeting of a Foreign Protein to Chloroplasts by Fusion to the Transit Peptide from the Samll Subunit of Ribulose 1,5-bisphosphate carboxylase." *Nature* (1985) vol. 313: 358-363.

Verwoerd TC., et al., "A Small-Scale Procedure for the Rapid Isolation of Plant RNAs." *Nuclic Acid Research* (1989) vol. 17: 2362.

Vincent MJ., et al., "Function of the KKXX (SEQ ID No. 3) Motif in Endoplasmic Reticulum Retrieval of a Transmembrane Protein Depends on the Length and Structure of the Cytoplamic Domain." *J. Biol. Chem* (1998) vol. 273: 950-956.

Yao et al., (2003) *Plant Biotech. J.* vol. 1:221-229.

Zambryski, P., et al., "Ti Plasmid Vector for the Introduction of DNA into Plant Cells Without Alteration of Their Normal Regeneration Capacity." *EMBO J.* (1983) vol. 2: 2143.

Zeng, Qian-Chun, et al. "Obtainng Stem Borer-Resistant Homozygous Transgenic lines of Minghui 81 Harboring Novel *cry/Ac* Gene *via* Particle Bombardment." *Acta Genetica Sinica* (2002) vol. 29 No. 6: 519-524.

Zhang, Geng-Li, et al. "An Initial Study of Transgenic *Carica papaya* Used as a Kind of Vaccine for Anti-*Tuberculosis.*" *Acta Botanica Yunnanica* (2003) vol. 25. No. 2: 223-229.

Chinese Office Action from CN Appl. No. 200480041766.9 dated Oct. 11, 2010 (10 pages).

Indian Office Action from IN Appl. No. 4141/DELNP/2006 dated Sep. 27, 2010 (3 pages).

Japanese Office Action from JP Appl. No. 2006-544192 dated Oct. 5, 2010 (8 pages).

SEQUENCE LISTING

<160> NUMBER OF SEQ ID NOS: 12

<210> SEQ ID NO 1
<211> LENGTH: 837
<212> TYPE: DNA
<213> ORGANISM: Synechococcus elongatus ATCC #33912, deposited as
      Anacystis nidulans
<220> FEATURE:
<223> OTHER INFORMATION: delta-9 desaturase (des9, DSG), fatty acyl-CoA
      desaturase, fatty acid desaturase

<400> SEQUENCE: 1

```
atgacccttg ctatccgacc caagcttgcc ttcaactggc cgaccgccct gttcatggtc      60
gccattcaca ttggagcact gttagcgttc ctgccggcca actttaactg gcccgctgtg     120
ggcgtgatgg ttgcgctgta ttacattacc ggttgttttg gcatcaccct aggctggcac     180
cggctaattt cgcaccgtag ctttgaagtt cccaaatggc tggaatacgt gctggtgttc     240
tgtggcacct tggccatgca gcacggcccg atcgaatgga tcggtctgca ccgccaccat     300
cacctccact ctgaccaaga tgtcgatcac cacgactcca acaagggttt cctctggagt     360
cacttcctgt ggatgatcta cgaaattccg gcccgtacgg aagtagacaa gttcacgcgc     420
gatatcgctg cgaccctgt ctatcgcttc tttaacaaat atttcttcgg tgtccaagtc     480
ctactggggg tacttttgta cgcctggggc gaggcttggg ttggcaatgg ctggtctttc     540
gtcgtttggg ggatcttcgc ccgcttggtg gtggtctacc acgtcacttg gctggtgaac     600
agtgctaccc acaagtttgg ctaccgctcc catgagtctg cgaccagtc caccaactgc     660 tggtgggttg cccttctggc ctttggtgaa ggctggcaca caaccacca cgcctaccag     720 tactcggcac gtcatggcct gcagtggtgg gaatttgact tgacttggtt gatcatctgc     780
ggcctgaaga aggtgggtct ggctcgcaag atcaaagtgg cgtctccaaa caactaa      837
```

<210> SEQ ID NO 2
<211> LENGTH: 278
<212> TYPE: PRT
<213> ORGANISM: Synechococcus elongatus ATCC #33912, deposited as
      Anacystis nidulans
<220> FEATURE:
<223> OTHER INFORMATION: delta-9 desaturase (des9, DSG), fatty acyl-CoA
      desaturase, fatty acid desaturase

<400> SEQUENCE: 2

```
Met Thr Leu Ala Ile Arg Pro Lys Leu Ala Phe Asn Trp Pro Thr Ala
1               5                   10                  15

Leu Phe Met Val Ala Ile His Ile Gly Ala Leu Leu Ala Phe Leu Pro
            20                  25                  30

Ala Asn Phe Asn Trp Pro Ala Val Gly Val Met Val Ala Leu Tyr Tyr
        35                  40                  45

Ile Thr Gly Cys Phe Gly Ile Thr Leu Gly Trp His Arg Leu Ile Ser
    50                  55                  60

His Arg Ser Phe Glu Val Pro Lys Trp Leu Glu Tyr Val Leu Val Phe
65                  70                  75                  80

Cys Gly Thr Leu Ala Met Gln His Gly Pro Ile Glu Trp Ile Gly Leu
                85                  90                  95

His Arg His His His Leu His Ser Asp Gln Asp Val Asp His His Asp
            100                 105                 110

Ser Asn Lys Gly Phe Leu Trp Ser His Phe Leu Trp Met Ile Tyr Glu
        115                 120                 125
```

```
Ile Pro Ala Arg Thr Glu Val Asp Lys Phe Thr Arg Asp Ile Ala Gly
            130                 135                 140

Asp Pro Val Tyr Arg Phe Asn Lys Tyr Phe Gly Val Gln Val
145                 150                 155                 160

Leu Leu Gly Val Leu Leu Tyr Ala Trp Gly Glu Ala Trp Val Gly Asn
                165                 170                 175

Gly Trp Ser Phe Val Val Trp Gly Ile Phe Ala Arg Leu Val Val Val
            180                 185                 190

Tyr His Val Thr Trp Leu Val Asn Ser Ala Thr His Lys Phe Gly Tyr
        195                 200                 205

Arg Ser His Glu Ser Gly Asp Gln Ser Thr Asn Cys Trp Trp Val Ala
    210                 215                 220

Leu Leu Ala Phe Gly Glu Gly Trp His Asn Asn His His Ala Tyr Gln
225                 230                 235                 240

Tyr Ser Ala Arg His Gly Leu Gln Trp Trp Glu Phe Asp Leu Thr Trp
                245                 250                 255

Leu Ile Ile Cys Gly Leu Lys Lys Val Gly Leu Ala Arg Lys Ile Lys
            260                 265                 270

Val Ala Ser Pro Asn Asn
        275

<210> SEQ ID NO 3
<211> LENGTH: 4
<212> TYPE: PRT
<213> ORGANISM: artificial
<220> FEATURE:
<223> OTHER INFORMATION: endoplasmic reticulum retention and retrieval
      signal sequence
<220> FEATURE:
<221> NAME/KEY: MOD_RES
<222> LOCATION: (3)..(4)
<223> OTHER INFORMATION: Xaa is any amino acid

<400> SEQUENCE: 3

Lys Lys Xaa Xaa
1

<210> SEQ ID NO 4
<211> LENGTH: 4
<212> TYPE: PRT
<213> ORGANISM: artificial
<220> FEATURE:
<223> OTHER INFORMATION: endoplasmic reticulum retention and retrieval
      signal sequence

<400> SEQUENCE: 4

Lys Asp Glu Leu
1

<210> SEQ ID NO 5
<211> LENGTH: 4
<212> TYPE: PRT
<213> ORGANISM: artificial
<220> FEATURE:
<223> OTHER INFORMATION: endoplasmic reticulum retention and retrieval
      signal sequence

<400> SEQUENCE: 5

Lys Lys Ser Ser
1

<210> SEQ ID NO 6
<211> LENGTH: 4
<212> TYPE: PRT
```

-continued

```
<213> ORGANISM: artificial
<220> FEATURE:
<223> OTHER INFORMATION: endoplasmic reticulum retention and retrieval
      signal sequence

<400> SEQUENCE: 6

His Asp Glu Phe
1

<210> SEQ ID NO 7
<211> LENGTH: 4
<212> TYPE: PRT
<213> ORGANISM: artificial
<220> FEATURE:
<223> OTHER INFORMATION: endoplasmic reticulum retention and retrieval
      signal sequence

<400> SEQUENCE: 7

Lys Glu Glu Leu
1

<210> SEQ ID NO 8
<211> LENGTH: 4
<212> TYPE: PRT
<213> ORGANISM: artificial
<220> FEATURE:
<223> OTHER INFORMATION: endoplasmic reticulum retention and retrieval
      signal sequence

<400> SEQUENCE: 8

Lys Asp Gln Leu
1

<210> SEQ ID NO 9
<211> LENGTH: 35
<212> TYPE: DNA
<213> ORGANISM: artificial
<220> FEATURE:
<223> OTHER INFORMATION: amplification primer DSG-XhoI-5'

<400> SEQUENCE: 9
cccccctcga gatgacccct tgctatccga cccaag                              35

<210> SEQ ID NO 10
<211> LENGTH: 36
<212> TYPE: DNA
<213> ORGANISM: artificial
<220> FEATURE:
<223> OTHER INFORMATION: amplification primer DSG-XhoI-3'

<400> SEQUENCE: 10
cccccctcga gttagttgtt tggagacgcc actttg                              36

<210> SEQ ID NO 11
<211> LENGTH: 45
<212> TYPE: DNA
<213> ORGANISM: artificial
<220> FEATURE:
<223> OTHER INFORMATION: amplification primer des9-3'-ER

<400> SEQUENCE: 11
ccccccctcg agttaagaag acttttttgtt gtttggagac gccac                   45

<210> SEQ ID NO 12
<211> LENGTH: 4
<212> TYPE: PRT
<213> ORGANISM: artificial
<220> FEATURE:
```

```
<223> OTHER INFORMATION: endoplasmic reticulum retention and retrieval
      signal sequence
<220> FEATURE:
<221> NAME/KEY: MOD_RES
<222> LOCATION: (3)..(4)
<223> OTHER INFORMATION: Xaa is any amino acid other than Ser

<400> SEQUENCE: 12

Lys Lys Xaa Xaa
1
```

TRANSGENIC PLANTS WITH REDUCED LEVEL OF SATURATED FATTY ACID AND METHODS FOR MAKING THEM

CROSS-REFERENCE TO RELATED APPLICATIONS

This application claims priority from Canadian patent application number 2,450,000 entitled "METHOD OF CREATING PLANTS WITH REDUCED LEVEL OF SATURATED FATTY ACID IN SEED OIL", filed Dec. 18, 2003.

FIELD OF THE INVENTION

This present invention relates generally to the field of transgenic plants. More specifically, the present invention relates to molecular technology for altering fatty acid metabolism in a plant, for lowering the saturated fatty acid content of the seed oil produced by such plant. This technology finds utility for example in commercial production of seed oil having improved nutritional value from oil-producing plants.

BACKGROUND OF THE INVENTION

There has been significant interest in altering fatty acid (FA) metabolism in plants in order to create plant-derived oils designed for specific purposes. The properties of the oil are determined by its fatty acid composition, which affects both nutritional composition and oxidative stability.

The level of saturated FAs in various types of fats and oils is a major health concern. Hence, there has been increasing pressure in the market to provide plant oils with lower saturated FA content. The main components of saturated fatty acid in most vegetable oil are 16:0 (palmitic acid) and 18:0 (stearic acid).

In the vegetable oil market, oil having less than 7% saturated FA content can be labeled "low-sat" and oil having less than 3.5% saturated FA content can be labelled "no-sat". Canola (*Brassica napus*) seed oil is typically low in saturated fatty acid, but it is difficult to keep the saturated fatty acid level below the "low-sat" threshold of 7% saturated FA content.

Previous attempts have been made to address this problem. For example, transgenic plants have been made that contain heterologous plant genes involved in fatty acid metabolism (see for example: Shah S, Weselake R (2003) Farming For the Future, AARI project #19990032, Final Report, pp. 1-82; and Yao et al. Plant Biotech J 2003, 1:221). However, these transgenic plants showed little or no reduction of saturated fatty acid in the transgenic plant. For example, Yao et al. (2003) report a 1 to 2% decrease in saturated FA level associated with expression of the ADS1 gene from *Arabidopsis* in *B. juncea* seeds.

In this context, prokaryotic genes provide an attractive alternative to plant genes, however prokaryotic proteins often show limited or no activity in a plant background (see e.g. Hahn J J, Eschenlauer A C, Narrol M H, Somers D A, Srienc F (1997) Growth kinetics, nutrient uptake, and expression of the *Alcaligenes eutrophus* poly(β-hydroxybutyrate) synthesis pathway in transgenic maize cell suspension cultures. Biotech Prog 13: 347-354).

It has been shown previously that the nutritional value of plant seed oil can be improved by making transgenic plants that express a heterologous delta-6 desaturase enzyme (derived from cyanobacteria, borage, or evening primrose) to effect the conversion of linoleic acid (ClsA9, 12), a polyunsaturated fatty acid, to gamma-linolenic acid (GLA, Cl8A6, 9,12) (see U.S. Pat. Nos. 5,552,306; 5,614,393; 5,663,068; 5,689,050 5,789,220; 6,355,861; 6,683,232; and us patent application publication No.: 20040078845). Linoleic acid (ClsA9,12) is an LO essential dietary constituent that cannot be synthesized by vertebrates and is usually obtained from plant sources; vertebrate cells can introduce double bonds at the delta-9 position of fatty acids but cannot introduce additional double bonds between the delta-9 double bond and the methyl-15 terminus of the fatty acid chain. Linoleic acid can be converted by mammals to gamma-linolenic acid (GLA, ClsA6,9,12), which in turn can be converted to arachidonic acid (20:4), an essential precursor of most prostaglandins.

Accordingly, there remains a need for transgenic plants that can provide seed oil having lower levels of saturated fatty acids.

SUMMARY OF THE INVENTION

The present invention provides molecular technology for reducing the levels of saturated fatty acids in seed oil produced by a plant. Specifically, the present molecular technology expresses in a plant an enzyme having delta-9 desaturase activity (i.e. that desaturates fatty acids at the delta-9 position) at a level effective for reducing the saturated fatty acid content in the seed oil produced by the plant.

Thus, in one aspect the present invention provides a recombinant polypeptide comprising a delta-9 desaturase enzyme from a prokaryote in operable linkage with an endoplasmic reticulum retention and retrieval signal sequence.
The delta-9 desaturase enzyme is from a prokaryote, such as a cyanobacterium, e.g. *Anacystis nidulans*.

In an embodiment, the delta-9 desaturase enzyme comprises:
(a) a polypeptide having the amino acid sequence set forth in SEQ ID NO:2;
(b) a variant or homologue of the polypeptide defined in (a) having at least 50%, 60%, 70%, 75%, 80%, 85%, 90%, or 95% identity thereto and having delta-9 desaturase activity; and
(c) a fragment of the polypeptide defined in (a) having at least 50 contiguous amino acids identical thereto and having delta-9 desaturase activity.

In one embodiment, the delta-9 desaturase enzyme comprises a polypeptide having the amino acid sequence set forth in SEQ ID NO:2, and the endoplasmic reticulum membrane retention and retrieval signal has the amino acid sequence KKSS (SEQ ID NO:5).

The present invention also provides: a nucleic acid molecule encoding the recombinant polypeptide defined above; a vector comprising such nucleic acid molecule in operable linkage with a promoter; a host cell transformed with such vector; and a transgenic plant cell comprising a transgenic element containing the nucleic acid molecule describe above, in operable linkage with a promoter which effects expression of the recombinant polypeptide in said transgenic plant cell.

The invention further provides a method of making a transgenic plant comprising: (a) transforming a plant cell with the nucleic acid molecule described above, or a vector comprising such nucleic acid, wherein said nucleic acid is in operable linkage with a promoter which effects expression of the recombinant polypeptide in said plant cell; and (b) regenerating a plant from the transformed plant cell produced in step (a).

The invention further provides a transgenic plant comprising a transgenic element containing the nucleic acid molecule described above in operable linkage with a promoter which effects expression of the recombinant polypeptide in said transgenic plant.

The transgenic plants and plant cells of the invention find utility, for example, in the production of seed oil having a reduced saturated fatty acid content as compared to a wild-type plant of the same species.

DETAILED DESCRIPTION

As an example of the invention, applicant developed transgenic canola plants demonstrating an about 40% reduction in % saturated fatty acid content as compared to current commercial cultivars. This was achieved by expressing in canola plants a recombinant polypeptide comprising a delta-9 desaturase enzyme of SEQ ID NO:2 fused to KKSS (SEQ ID NO:5), an endoplasmic reticulum (ER) retrieval and retention signal. Applicant found that expression of the desaturase delta-9 enzyme fused to KKSS (SEQ ID NO:5) provided a significant reduction in saturated FA content of canola seed oil, whereas the desaturase gene alone (i.e. not fused to KKSS (SEQ ID NO:5)) is less effective in reducing saturated fatty acid level in canola seed oil. Compared to about 7.2% saturated fatty acid content in seed oil from wild-type canola, the transgenic canola lines described herein contain as low as about 4.3% saturated fatty acids. Both major saturated fatty acids (16:0 and 18:0) in canola were reduced in these lines.

In the present context, the position of a double bond in a fatty acid is indicated after the symbol "Δ (delta)" by the number of carbons from the carboxy terminus to the carbon having the double bond. The total number of double bonds is indicated after a colon following the total number of carbons. For example, linoleic acid is designated as $18:2\Delta^{9,12}$, which is represented by the following structural formula: $CH_3(CH_2)_4 CH=CHCH_2CH=CH(CH_2)_7COOH$. However there are other conventions for naming fatty acids used in the art, e.g. the position of a double bond may be indicated after the symbol "ω (omega)" by the number of carbons from the methyl terminus of a fatty acid to the carbon having the double bond.

In the present context, a "polypeptide of the invention" is a recombinant polypeptide having a delta-9 desaturase enzyme from a prokaryote in operable linkage with an endoplasmic reticulum retention and retrieval signal sequence.

In the present context, a "nucleic acid molecule of the invention" is a recombinant nucleic acid molecule encoding a polypeptide of the invention.

In the present context, a "wild-type" plant or plant cell is one that has not been engineered to express a polypeptide of the invention.

In the present context, "delta-9 desaturase activity" means the capacity to introduce a double bond at the delta-9 position of a saturated fatty acid, such as a 16:0, 18:0, 20:0 or 22:0 saturated fatty acids or any combination thereof.

The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

Delta-9 Desaturase Enzymes

The delta-9 desaturase enzyme used in the present examples is from *Anacystis nidulans*, a cyanobacterium (Ishizaki-Nishizawa et al. 1996) and has the amino acid sequence set forth in SEQ ID NO:2. This protein introduces a cis-double bond (or desaturation) at the delta-9 position of saturated fatty acids bound to lipids. It has higher specificity for 16:0 fatty acids but also desaturates larger saturated fatty acids, such as 18:0. This protein is described in detail in U.S. Pat. No. 6,043,411 to Nishizawa et al.; in Nature Biotechnology 14: 1003-1006 and registered in EMBL GeneBank as accession number X77367, all of which references are incorporated herein by reference. The gene encoding this desaturase is referred to herein as the "des9 gene (SEQ ID NO:1) from *Anacystis nidulans*" but is sometimes referred to in the art as the DSG gene.

Delta-9 desaturase enzymes from other prokaryotic sources can be used in the present invention. For example, suitable prokaryotic sources of delta-9 desaturase enzymes that may be useful in the present invention include but are not limited to bacteria, e.g. cyanobacteria belonging to the genera *Anacystis, Synechocystis, Anabaena, Aphanocapsa, Mastigocladus, Nitzchia, Synechococcus,* and *Spirulina.*

Higher plants contain a larger amount of 16:0 FA than 18:0 FA. Therefore, delta-9 desaturase enzymes with a high affinity for 16:0 FA substrates are preferred for practicing the invention.

The delta-9 desaturase enzyme component of the polypeptide of the invention may be a variant of a native delta-9 desaturase enzyme, for example: deletions, including truncations and fragments; insertions and additions, including tagged polypeptides and fusion proteins; and substitutions, for example site-directed mutants and allelic variants. Variants can be prepared, for example, by substituting, deleting or adding one or more amino acid residues in the amino acid sequence of a native delta-9 desaturase enzyme or fragment thereof, and screening for biological activity.

Suitable variants for practising the invention may have for example at least 50%, 60%, 70%, 75%, 80%, 85%, 90%, or 95% identity to a native desaturase and have delta-9 desaturase activity.

The delta-9 desaturase enzyme can also be a homologue of a known delta-9 desaturase enzyme (such as the delta-9 desaturase enzyme (SEQ ID NO:2) from *Anacystis nidulans*). Homologues can be identified using standard molecular biology techniques or by searching for homologous sequences deposited in genetic databases.

Suitable homologues for practising the invention may have for example at least 50%, 60%, 70%, 75%, 80%, 85%, 90%, or 95% identity to a native desaturase (such as delta-9 desaturase enzyme (SEQ ID NO:2) from *Anacystis nidulans*) and have delta-9 desaturase activity.

Suitable fragments for practising the invention may have at least 50 contiguous amino acids identical to a native delta-9 desaturase enzyme and have delta-9 desaturase activity. For example, suitable fragments can have at least about 50, 100, 150, 200, or 250 contiguous amino acids identical to a native delta-9 desaturase enzyme.

Endoplasmic Reticulum Retention And Retrieval Signals

In oil-producing plants, oil synthesis and desaturation of the lipid bound fatty acids take place in the ER of the cells, particularly in seeds. Therefore, it may be possible to increase the activity of a prokaryotic enzyme involved in fatty acid metabolism (such as a desaturase) in a eukaryotic cell by targeting the enzyme to the ER.

Many transmembrane proteins are processed and transported to the cell surface in eukaryotic cells. Some of these proteins can be retrieved and retained in the endoplasmic reticulum (ER) by adding a suitable signal sequence to the protein. For example, the following amino acid sequences can function as ER retention and retrieval signal sequences:

(a) KDEL (SEQ ID NO:4) (see for example Van den Broeck et al. (1985) Nature 313, 358; and Michaelis et al. (1982) Ann. Rev. Microbiol. 36, 425);

(a) KKXX (SEQ ID NO:3), wherein X is any amino acid, in particular KKSS (SEQ ID NO:5) (Vincent et al. (1998) J. Biol. Chem. 273:950-6);

b) HDEF (SEQ ID NO:6) (Lehmann K. et al. (2001) Plant Physiol. October; 127(2): 436-49);

(c) KEEL (SEQ ID NO:7) and KDQL (SEQ ID NO:8) (Manabu Murakami, Takayoshi Ohba, Feng Xu, Seiji Shida, Eisaku Satoh, Kyoichi Ono, Ichiro Miyoshi, Hiroyuki Watanabe, Hiroshi Ito, and Toshihiko Iijima "Genomic organization and functional analysis of murine PKD2L1" (2004) JBC Papers in Press. Published Nov. 17, 2004 as Manuscript number M411496200).

The present examples demonstrate that the activity of a prokaryotic delta-9 desaturase enzyme (e.g. SEQ ID NO: 2) in a plant (e.g. canola) can be increased by linking this enzyme operably to an ER retention and retrieval signal sequence (e.g. KKSS (SEQ ID NO:5)), to provide a significant reduction in the levels of saturated fatty acids in seed oil produced by the plant.

Although the present examples use KKSS (SEQ ID NO:5) as the ER retention and retrieval signal sequence, other ER retention and retrieval signal sequences (such as KKXX where X is an amino acid other than "S" (SEQ ID NO:12)) can be used to retrieve and retain the protein in the ER. The scope of this invention is not limited to any particular prokaryotic delta-9 desaturase enzyme or any particular signal sequence, or any particular combination thereof. That is, other delta-9 desaturase enzymes and other ER retention and retrieval signal sequences may be used in the present invention.

Thus, examples of suitable ER retention and retrieval signal sequences for practising the invention include but are not limited to: KDEL (SEQ ID NO:4), KKSS (SEQ ID NO:5), HDEF (SEQ ID NO:6); KEEL (SEQ ID NO:7) and KDQL (SEQ ID NO:8).

The term 'operably linked' means that the regulatory sequences necessary for expression of the coding sequences and the ER retrieval and retention signal sequences are placed in the DNA construct in the appropriate position relative to the coding sequence and in correct reading frame so as to effect expression of the gene.

To be in operative linkage, ER retention and retrieval signal sequence is added to the carboxy terminal of the delta-9 desaturase enzyme. The ER retention and retrieval signal sequence can be at the extreme carboxy terminal portion of the polypeptide of the invention, or it may be followed by additional amino acids. The signal sequence may be added by genetic engineering of the gene that codes for the delta-9 desaturase enzyme.

Nucleic Acid Molecules

The term "DNA construct" refers here to a genetic DNA sequence used to transform cells.

The term "expression cassette" refers here to a sequence of DNA comprised of a coding region to which promoter and terminator regulatory sequences have been linked at the 5' and 3' end to achieve proper expression of the gene as well as the gene product in a transformed plant cell.

In the present examples, Applicant assembled a DNA construct, which contained two expression cassettes: a first cassette comprising the des9 gene of *Anacystis nidulans* (SEQ ID NO:1) operably linked to a nucleotide sequence encoding the signal KKSS (SEQ ID NO:5), the seed specific napin promoter from *Brassica*, and the rbcs3' transcription terminator from pea; and a second expression cassette comprising a promoter, coding region and terminator expressing a gene product suitable to aid in the identification and selection of transformed plant cells and plants. The second expression cassette is optional, as other methods may be used to identify and select transformants.

Selection can be carried out using any suitable selection means, such as: antibiotic selection (e.g. kanamycin, gentamycin, hygromycin); metabolic marker genes for specific sugars that are not present in plants (e.g. the Positech™ selection system from Syngenta; and phosphomannose isomerase); herbicidal marker genes (e.g. pat and bar from Bayer and EPSPS from Monsanto); visible selection markers, e.g. green fluorescent protein; etc. In the present case, selection was carried out using kanamycin resistance.

In the present embodiment, applicant used the powerful seed-specific storage protein napin promoter. However other seed-specific promoters can be used in the present invention include, including but not limited to: cruciferin promoter; hydroxylase promoter; legumin promoter (Shasany A K et al. (2000) Indian J Exp Biol. April; 38(4): 363-72); phaseolin promoter; and zein promoter. It may be possible to use a promoter that is not seed-specific, but such a promoter may not be as effective at reducing the saturated FA content of plant seed oil product.

In the present example, the coding region is also operably linked at the 3' end with the rbcs3' transcription terminator as a regulatory sequence. Other useful 3' regulatory regions which can also be used in the present invention include, but are not limited to: nopaline synthetase polyadenylation region (NOS) and octopine polyadenylation region. (OCS).

The DNA construct may be conveniently built in a first vector suitable for propagation in a bacterial host, then excised and ligated into a second vector for introduction into a plant host. Examples of suitable vectors for introduction into a plant host include the pCAMBIA series of vectors (Center for the Application of Molecular Biology to International Agriculture (CAMBIA)) and the pBI series of vectors (BD Biosciences Clontech), as well as pKYLX71-based vectors (Scharld et al. (1987)). Choice of vector will depend in part on the intended mechanism of transformation, i.e. *Agrobacterium* mediated transformation or direct gene transfer.

Transformed and Transgenic Plants and Plant Cells

Transformed plant cells and transgenic plants comprising the nucleic acid of the invention can be generated using any methods of DNA delivery known to those skilled in the art (see for example "Plant genetic transformation and gene expression; a laboratory manual", Draper J. et al. Eds. Blackwell Scientific Publications, 1988). These include, but are not limited to: *Agrobacterium*-mediated transfection; biolistic DNA delivery; electroporation of protoplasts; direct DNA uptake; PEG treatment of protoplast; UV laser microbeam; Gemini virus vectors; liposome-mediated DNA uptake; calcium phosphate treatment of protoplasts; and agitation of cell suspensions with microbeads coated with the transforming DNA. Among these, the use of *Agrobacterium* is preferred for dicotyledonous plants such as canola since it secures stable transformation. The methods using *Agrobacterium* include an intermediate vector method using a wild-type tumor plasmid (nature, 287 (1980) p. 654; Cell, 32 (1983) p. 1033; EMBO J., 3 (1984) p. 1525), an intermediate vector method using a vector deficient of a tumor formation gene region of T-DNA (EMBO J., 2 (1983) p. 2143; Bio/Technoloy, 3 (1985) p. 629), a binary vector method (Bio/Technology, 1 (1983) p. 262; Nature, 303 (1983) p. 179; Nucl. Acids Res., 12 (1984) p. 8711) and the like. Any of these methods can be used. Methods in which plants are infected with *Agrobacterium* include direct inoculation to cultured cells, protoplast co-cultivation, and a leaf-disk method. A leaf-disk method is convenient in many cases for producing a large number of transformed plants in a direct and easy way.

Plants can be regenerated by culturing transformed plant cells in known media such as Murashige-Skooge medium that may be supplemented with selection antibiotics and/or plant growth hormones. Rooted seedlings are transplanted into soil and cultured for growth into regenerated plants.

In the examples described below, the DNA construct described above was introduced into the genome of canola plants using *Agrobacterium* T-DNA mediated plant transformation. Briefly, using the *Agrobacterium* binary vector system, the transformation of plant nuclei was accomplished by: a) inserting the des9 gene (SEQ ID NO:1) from *Anacystis nidulans* and the retrieval and retention signal KKSS (SEQ ID NO:5) into a vector, b) introducing the vector into *Agrobacterium*; c) co-cultivating cotyledons excised from young seedlings with a suspension of recombinant *Agrobacterium* followed by incubation in non-selective medium, d) transferring the plant tissues into selective medium to identify transformed tissue, e) identifying transformed tissue and f) regenerating plants from the transformed tissue.

The level of expression of the transgenes can vary depending on the position and number of their insertion into the nuclear genome. Therefore, several transformants should be regenerated and tested for expression of the transgene and for altered fatty acid profile. Fatty acid profiles can be assayed by any suitable technique in the art, such as:

(a) Gas Chromatography (GC): fatty acids methyl esters (FAME), butyl/butanol esters, propan-2-ol esters (See, for example, the International Organization for Standardization method reference number ISO 5508:1990 (E), "Animal and vegetable fats and oils—Analysis by gas chromatography of methyl esters of fatty acids");
(b) High-Performance liquid Chromatography (HPLC): adsorption chromatography, chiral chromatography, silver-ion chromatography, reversed-phase chromatography;
(c) Mass-Spectrometry (MS): picolinyl esters, dimethyloxazolines (DMOX), pyrrolidides, dimethyl disulphide derivatives;
(d) Infrared Spectroscopy (IR); and
(e) Fourier Transform Infrared Spectroscopy (FTIR).

In general only those transgenic plants that demonstrate a significant reduction in saturated fatty acid content of their seed oil (i.e. where the saturated fatty acid content of the seed oil is reduced by about 10%, about 15%, about 20%, about 30%, about 40% about 50% or more as compared to a wild-type plant of the same species) are desired and will be selected for further cultivation.

The present examples demonstrate transformation of canola (*Brassica napus*) with the cyanobacterial delta-9 desaturase enzyme operably linked with the ER retrieval and retention signal resulting in reduction of total saturated fatty acid content in seed oil. However, the biochemistry of oil synthesis (e.g. desaturation of fatty acids) and sub-cellular localization of these metabolic reactions is similar in other oil seed crops. Therefore, the present molecular technology may be applied to other oil seed plants, both dicotyledonous and monocotyledonous, including but not limited to: soybean, corn, peanut, sunflower, olive, palm, coconut, safflower, cottonseed, mustard, sesame, hemp, castor, avocado and flax.

The present invention also provides cells and tissues (in particular, seeds) of the aforementioned transgenic plants.

The aforementioned transgenic plants and their progeny can be used to transfer the gene of interest into other genotypes, cultivars, varieties and the like, through cross-breeding and selection. Thus the molecular technology advanced by the current invention can be used to generate a great variety of hybrid plants carrying the recombinant nucleic acid of the invention, for producing seed oil having reduced levels of saturated fatty acids.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

The present invention will now be explained in greater detail by the following examples, which are by no means intended to limit the scope of the invention.

EXAMPLES

Example 1

Gene Construct without ER Signal

The open reading frame (ORF) of the des9 gene (SEQ ID NO:1; 837 bp) was amplified from *Anacystis nidulans* (*Synechococcus* sp., ATCC # 33912) using primers:

```
DSG-XhoI-5':
CCCCCCTCGAGATGACCCTTGCTATCCGACCCAAG   (SEQ ID NO: 9)
and

DSG-XhoI-3':
CCCCCCTCGAGTTAGTTGTTTGGAGACGCCACTTTG  (SEQ ID NO: 10)
``` with XhoI site introduced in both primers immediately outside start and stop codon. The PCR product was gel purified, digested with XhoI and ligated to *E. coli* vector pBluescript (BS/KS) and sequenced to confirm its identity. The des9 gene (SEQ ID NO:1) was then excised from BS/KS by XhoI and ligated into plant vector pKYLX-Napin. This vector was created by replacing the double 35S promoter of vector pKYLX71 (Scharld et al. 1987) with the seed-specific Napin promoter from *Brassica napus*. Several recombinant vectors were analyzed by restriction digestion to identify clone having correct orientation of the des9 gene insert in respect to the promoter and the terminator. The recombinant vector (pC7)

was sequenced to confirm proper ligation and no rearrangement of the introduced des9 gene insert in the plant vector.

Example 2

Gene Construct with ER Signal

The ORF (837 bp) of des9 gene (SEQ ID NO:1) was amplified from *Anacystis nidulans* (*Synechococcus* sp., ATCC # 33912) using primers:

```
DSG-XhoI-5':
                                    (SEQ ID NO: 9)
CCCCCCTCGAGATGACCCTTGCTATCCGACCCAAG
and des9-3'-ER:
                                    (SEQ ID NO: 11)
CCCCCCCTCGAGTTAAGAAGACTTTTTGTTGTTTGGAGACGCCAC
``` with XhoI site introduced in both primers immediately outside start and stop codon. In des9-3'-ER primer, the stop codon of the des9 gene was converted to amino acid K and three more amino acids were added afterward (KSS) followed by a new stop codon and an XhoI site. The PCR product (now 849 bp due to addition of 4 amino acids) was gel purified, digested with XhoI, ligated to BS/KS and sequenced to confirm its identity. The des9 gene was then excised from BS/KS by XhoI and ligated into plant vector pKYLX-Napin. Several recombinant vectors were analyzed to identify clone having correct orientation of the des9 gene insert in respect to the promoter and the terminator. The recombinant vector (pC8) was sequenced to confirm proper ligation and no rearrangement of the introduced des9 gene insert in the plant vector.

Example 3

Introduction of Vectors into *Agrobacterium*

Both constructs (pC7 and pC8) were then transferred from *E. coli* strain DH5α to *Agrobacterium tumefacience* strain GV3101 by triparental mating. pRK2013 in *E. coli* HB101 was used as helper plasmid (Ditta et al., 1980). Transconjugants were selected for several cycles on 50 mg/L rifampicin, 20 mg/L gentamicin and 15 mg/L tetracycline plates. To ascertain that no rearrangement had taken place, plasmids were extracted from transconjugants, digested with restriction endonucleases and compared to the plasmid purified from *E. coli* DH5α.

Example 4

Canola Transformation

Canola cultivar 'Wester' was transformed with pC7 and pC8 gene constructs using protocol developed by Moloney et al. (1989). In brief, fully unfolded cotyledons from five days old seedlings were cut off including petiole with a sharp knife as close to the apical meristem as possible without including it. The cut end of the petiole was dipped briefly into a 1 ml liquid culture of *Agrobacterium tumefaciens* harboring the des9 gene construct (O.D. of approx. 0.5). The petioles were then embedded into MMO-BA co-cultivation medium [Murashige Minimal Organics (MMO, Invitrogen Corp., Burlington, Canada) with Benzyle adenine (BA)] in petri plates so that explants stand up vertical. The plates were sealed with surgical tape and kept in growth room at 25 C with 16 h light/8 h dark, 70-80 mE for 2-3 days. Callus was induced by transferring the explants into MMO-BA medium containing 300 mg/L Timentin (GlaxoSmithKline, Missisauga, Canada).

Example 5

Selection and Regeneration of Complete Plants

Shoot formation from the callus was induced by transferring the explants into plates of MMO-BA medium containing 300 mg/L Timentin and 20 mg/L Kanamycin. These shoots were cut off from the explants and put into magenta vessels containing MMO medium with antibiotics (but without BA) for shoot development. When the shoots grew out with normal morphology and apical dominance, they were transferred to root induction medium [Murashige and Skoog (MS) medium containing antibiotics and Napthalene acetic acid (NAA)]. Once a good root system has formed, the plants were removed from the vessel, most of the agar cleaned off under running water and transferred to moist potting soil, covered with jars to avoid drying. They were then put into a humidity chamber and the covering was slowly removed to allow more air in, hardening off the plant.

Example 6

Characterization of Transformants

Regenerated plants were identified as transgenic by polymerase chain reaction (PCR) using des9 gene specific primers. Embryos of T1 seeds from regenerated transformed plants were chopped into smaller pieces and placed in a selection plate containing kanamycin. Embryos from transgenic plants were either all green or a combination of green and pale (the ratio depending upon the number of transgenes integrated) while seeds from non-transgenic plants were all pale. This was because the binary vector was engineered to carry a neomycin phosphotransferase (NptII) gene in tandem with the des9 gene.

Integration of the des9 gene into the canola genome was confirmed through Southern blot analysis. Genomic DNA from young leaves was isolated following Dellaporta et al. (1983). Ten µg of genomic DNA was digested with a restriction enzyme that cut only in one end of the expression cassette in the binary vector. The digested DNA was then electrophoresed on a 1% agarose gel, transferred to nylon membrane following the manufacturer's instruction (Amersham Canada Ltd., Oakville, ON) and probed with des9 gene labeled with [α-32P]-dCTP by random prime labeling (Life Technologies, Grand Island, N.Y.). Hybridization and washing of the blot at 65° C. was performed following Sambrook et al. 1989.

Expression of the des9 gene in the transgenic canola plants was confirmed through RNA analysis by RT-PCR and Northern blot. Total RNA was extracted from young leaves following procedure described in Verwoerd et al. (1989). The RNA was electrophoresed on a formaldehyde-containing agarose gel, blotted on a nylon membrane and hybridized with the des9 gene probe. The hybridization and washing condition was same as Southern hybridization.

Example 7

Fatty Acid Analysis of Seeds

Fatty acid composition of total acyl lipid from mature seeds was determined following the International Organization for Standardization method reference number ISO 5508:1990 (E), "Animal and vegetable fats and oils—Analysis by gas chromatography of methyl esters of fatty acids". Between 50 and 100 mg of seeds were crushed in 1 mL of petroleum ether in a 5 mL polypropylene vial using a steel rod. After allowing the meal to settle, 0.5 mL of supernatant was transferred to a glass tube containing 1.2 mL of methylating solution (2% sodium methoxide in methanol). After thorough mixing, the solution was incubated at room temperature for 30 minutes. One mL of ddH2O was added to the solution, mixed well and left for 10 minutes at room temperature for the phases to separate. After separation, 200 µL from the upper layer was diluted with another 300 µL of petroleum ether in a GC autosampler vial and 1 µL was injected into a GC column.

Separation of FAMEs was performed on a flame ionization gas chromatograph (model 6890, Hewlett Packard, Mississauga, ON) fitted with a 30-m×0.25 mm (i.d.) column (HP-INNOWAX, crosslinked polyethylene glycol) with helium as the carrier gas at a flow rate of 28.0 mL/minute. The oven temperature was from 180° C. to 230° C. at a rate of 5° C./minute and hold at 230° C. for 13 minutes. Peaks were assigned by comparing retention time of those of FAME standards and relative proportions of FAMEs were determined as percentages of summed peak areas.

TABLE 1

Fatty acid content (mol %) of seeds of transgenic canola plants carrying des9 gene (SEQ ID NO: 1) from *Anacystis nidulans* linked with nucleotide sequences encoding the KKSS (SEQ ID NO: 5) ER retrieval and retention signal (C8-19.1), transgenic plant carrying only the des9 gene (C7-15) and non-transformed plants (WT).

|    | 16:0 | 16:1 | 18:0 | 18:1 | 18:2 | 18:3 | 20:0 | 20:1 | 22:0 | 22:1 | Saturated |
|----|------|------|------|------|------|------|------|------|------|------|-----------|
| WT | 4.1  | 0.3  | 2.0  | 66.2 | 17.6 | 7.2  | 0.7  | 1.2  | 0.4  | 0.1  | 7.2       |
| C7 | 4.0  | 0.4  | 1.9  | 66.4 | 17.8 | 7.0  | 0.6  | 1.2  | 0.4  | 0.1  | 6.9       |
| C8 | 2.1  | 2.0  | 1.2  | 67.2 | 18.0 | 7.1  | 0.6  | 1.2  | 0.3  | 0.1  | 4.3       |

REFERENCES

"Plant genetic transformation and gene expression; a laboratory manual", Draper J. et al. Eds. Blackwell Scientific Publications, 1988.

Nature, 287 (1980) p. 654.

Cell, 32 (1983) p. 1033.

EMBO J., 3 (1984) p. 1525).

EMBO J., 2 (1983) p. 2143; Bio/Technoloy, 3 (1985) p. 629.

Bio/Technology, 1 (1983) p. 262.

Nature, 303 (1983) p. 179.

Nucl. Acids Res., 12 (1984) p. 8711.

Dellaporta S L, Wood J, Hicks J B (1983) A plant DNA mini-preparation: version II. Plant Mol Biol Rep 1: 19-21.

Ditta M. J., S. Stanfield, D. Corbin and D. R. Helsinki, 1980. Broad host range DNA cloning system for Gram negative construction of a gene bank of *Rhizobium meliloti*. Proc Natl Acad Sci USA 27, 7347-7351.

Hahn J J, Eschenlauer A C, Narrol M H, Somers D A, Srienc F (1997) Growth kinetics, nutrient uptake, and expression of the *Alcaligenes eutrophus* poly(β-hydroxybutyrate) synthesis pathway in transgenic maize cell suspension cultures. Biotech Prog 13: 347-354.

Horsch, R. B., J. Fry, N. Hofmann, J. Neidermeyer, S. G. Rogers and R. T. Fraley, 1988. Leaf disc transformation. Plant Molecular Biology Manual, A5/1-A5/9. Kluwer Academic Publishers, Dordrecht/Boston/London.

Lehmann K. et al. (2001) Plant Physiol. October; 127(2): 436-49.

Manabu Murakami, Takayoshi Ohba, Feng Xu, Seiji Shida, Eisaku Satoh, Kyoichi Ono, Ichiro Miyoshi, Hiroyuki Watanabe, Hiroshi Ito, and Toshihiko Iijima "Genomic organization and functional analysis of murine PKD2L1" (2004) JBC Papers in Press. Published Nov. 17, 2004 as Manuscript number M411496200.

Michaelis et al. (1982) Ann. Rev. Microbiol. 36, 425.

Moloney M, Walker J M and Sharma K K 1989 High efficiency transformation of *Brassica napus* using *Agrobacterium* vectors, Plant Cell Rep. 8, 238-242.

Nishizawa O, Toguri T (1996) Gene for fatty acid desaturase, vector containing said gene, plant transformed with said gene, and process for creating said plant. U.S. Pat. No. 6,043,411.

Nishizawa O, Fujii T, Azuma M, Sekiguchi K, Murata N, Ohtani T, Toguri T (1996) Low-temperature resistance of higher plants is significantly enhanced by a nonspecific cyanobacterial desaturase. Nature Biotechnology 14: 1003-1006.

Sambrook, J., E. F. Fritsch, and T. Maniatis, 1989. Molecular Cloning: A Laboratory Manual. Cold Spring Harbor Laboratory Press, Cold Spring Harbor, N.Y.

Schardl C. L., A. D. Byrd, G. Benzion, M. A. Altschuler, D. F. Hildebrand and A. G. Hunt, 1987. Design and construction of a versatile system for the expression of foreign genes in plants. Gene 61, 1-11.

Shah S, Weselake R (2003) Farming For the Future, AARI project #19990032, Final Report, pp. 1-82.

Shasany A K et al. (2000) Indian J Exp Biol. April; 38(4): 363-72.

Van den Broeck et al. (1985) Nature 313, 358.

Verwoerd T C, Dekker B M M and Hoekema A (1989) A small-scale procedure for the rapid isolation of plant RNAs. Nuclic Acid Research, 17: 2362.

Vincent M J, Martin A S, Compans R W (1998) Function of the KKXX (SEQ ID NO:3) motif in endoplasmic reticulum retrieval of a transmembrane protein depends on the length and structure of the cytoplasmic domain. J Biol Chem. 273:950-6.

U.S. Pat. No. 5,552,306.

U.S. Pat. No. 5,614,393.

U.S. Pat. No. 5,663,068.

U.S. Pat. Nos. 5,689,050 and 5,789,220.

U.S. Pat. No. 6,355,861.

U.S. Pat. No. 6,683,232.

US patent application publication No.: 20040078845.

The invention claimed is:

1. A nucleic acid molecule comprising a first nucleotide sequence encoding a delta-9 desaturase enzyme from *Anacystis nidulans* in operable linkage with a second nucleotide sequence linked to a 3' end of the first nucleotide sequence, the second nucleotide sequence encoding an endoplasmic reticulum membrane retention and retrieval signal sequence set forth in SEQ ID NO:3 or SEQ ID NO:5.

2. A nucleic acid molecule comprising the first nucleotide sequence encoding the delta-9 desaturase enzyme from *Anacystis nidulans* in claim 1, wherein the first nucleotide sequence comprises the amino acid sequence set forth in SEQ ID NO:2.

3. A vector comprising the nucleic acid molecule of claim 1 in operable linkage with a promoter.

4. A host cell transformed with the vector of claim 3.

5. The host cell of claim 4 that is derived from an oil seed plant.

6. The host cell of claim 5, wherein said oil seed plant is selected from the group consisting of canola, soybean, corn, peanut, sunflower, olive, palm, coconut, safflower, cottonseed, mustard, sesame, hemp, castor, avocado and flax.

7. The host cell of claim 5, wherein said oil seed plant is canola.

8. A transgenic plant comprising a transgenic element containing the nucleic acid molecule of claim 1 in operable linkage with a promoter which effects expression of the recombinant polypeptide in said transgenic plant.

9. A method for producing seed oil having a reduced saturated fatty acid content as compared to seed oil from a wild-type plant of the same species, the method comprising extracting oil from a transgenic plant of claim 8.

* * * * *